(12) United States Patent
Morere et al.

(10) Patent No.: US 8,597,706 B2
(45) Date of Patent: Dec. 3, 2013

(54) METHOD FOR SYNTHESIZING 2-ACETYL-1-PYRROLINE, STABLE KETAL PRECURSORS THEREOF, AND ISOTOPICALLY MARKED ANALOGS

(75) Inventors: Alain Morere, Les Matelles (FR); Chantal Menut, Saint Vincent de Barbeyrargues (FR); Yusuf Ziya Gunata, Montpellier (FR); Abdelhamid Agrebi, La Marsa (FR)

(73) Assignees: Centre National de la Recherche Scientifique (CNRS), Paris (FR); Universite Montpellier 2 Sciences et Techniques, Montpellier (FR)

( * ) Notice: Subject to any disclaimer, the term of this patent is extended or adjusted under 35 U.S.C. 154(b) by 0 days.

(21) Appl. No.: 13/380,268

(22) PCT Filed: Jun. 24, 2010

(86) PCT No.: PCT/EP2010/059007
§ 371 (c)(1),
(2), (4) Date: Dec. 22, 2011

(87) PCT Pub. No.: WO2010/149744
PCT Pub. Date: Dec. 29, 2010

(65) Prior Publication Data
US 2012/0100274 A1    Apr. 26, 2012

(30) Foreign Application Priority Data
Jun. 24, 2009  (FR) .................... 09 54319

(51) Int. Cl.
*A23L 1/226* (2006.01)
*C07D 407/10* (2006.01)
*C07D 207/08* (2006.01)
*C07D 207/10* (2006.01)
*C07D 207/20* (2006.01)

(52) U.S. Cl.
USPC ........... 426/537; 548/517; 548/540; 548/565; 548/570

(58) Field of Classification Search
USPC .......................... 548/574, 517; 546/248, 207
See application file for complete search history.

(56) References Cited

U.S. PATENT DOCUMENTS
6,723,856 B1   4/2004 Srinivas et al.

FOREIGN PATENT DOCUMENTS
DE   42 17 395 A1   12/1993
EP   0 436 481 A1    7/1991

OTHER PUBLICATIONS

Norman, M. H. and Heathcock, C. H. Novel Transformations Leading to 3-Benzylindolizidin-2-ones. J. Org. Chem. 1987, 52, 226-235.*

Naef, R. et al. Volatile Constituents of Semnostachya Menglaensis Tsui. J. Agric. Food Chem. 2005, 53, 9161-9164.*
Brambilla, R. et al. Intramolecular Cycloadditions of Nitrones Joined by Amides to Olefins. Tetrahedron 1981, 37, 3615-3625.*
Lepschy et al. "Dakin West Reaction. IV. Reaction of alpha-amino dicarboxylic acids with carboxylic anhydrides." Justus Lieb. Ann. Chem. 1974, 11, 1753-1762.*
Adams et al. Chem. Rev. 2006, 106, 2299-2319.*
Buttery, Ron G., et al., "Cooked Rice Aroma and 2-Acetyl-1-pyrroline," J. Agric. Food Chem., 1983, pp. 823-826, vol. 31.
De Kimpe, Norbert G., et al., "Synthesis of 2-Acetyl-1-pyrroline, the Principal Rice Flavor Component," J. Agric. Food Chem., 1993, pp. 1458-1461, vol. 41.
Hofmann, Thomas, et al., "New and Convenient Syntheses of the Important Roasty, Popcorn-like Smelling Food Aroma Compounds 2-Acetyl-1-pyrroline and 2-Acetyltetrahydropyridine from Their Corresponding Cyclic α-Amino Acids," J. Agric. Food Chem., 1998, pp. 616-619, vol. 46.
Hofmann, Thomas, et al., "2-Oxopropanal, Hydroxy-2-propanone, and 1-Pyrroline-Important Intermediates in the Generation of the Roast-Smelling Food Flavor Compounds 2-Acetyl-1-pyrroline and 2-Acetyltetrahydropyridine," J. Agric. Food Chem., 1998, pp. 2270-2277, vol. 46.
Yoshihashi, Tadashi, et al., "Precursors of 2-Acetyl-1-pyrroline, a Potent Flavor Compound of an Aromatic Rice Variety," J. Agric. Food Chem., 2002, pp. 2001-2004, vol. 50.
Fuganti et al., "A general method for the synthesis of the most powerful naturally occurring Maillard flavors," Tetrahedron, vol. 63, pp. 4762-4767, 2007.

(Continued)

*Primary Examiner* — Samantha Shterengarts
*Assistant Examiner* — Amanda L Aguirre
(74) *Attorney, Agent, or Firm* — Foley & Lardner LLP (57) ABSTRACT

The present invention relates to a method for synthetizing a compound of the following formula (I):

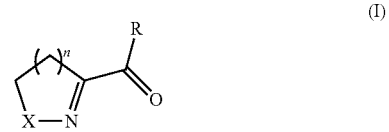

wherein R is a methyl or ethyl group, n is 1 or 2, and X is a $CH_2$ or $CD_2$ group, from a compound of the following formula (II):

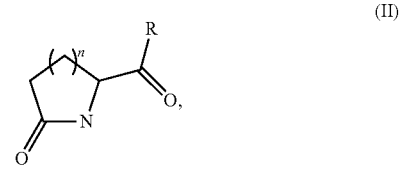

wherein R and n are as defined above,
and also relates to a method for assaying the compounds of the formula (I) using a corresponding deuterated derivative as an internal reference, as well as to the use of ketal derivatives of compounds of the formula (I) as a stable precursor, in particular in a flavoring composition.

11 Claims, 5 Drawing Sheets

(56) References Cited

OTHER PUBLICATIONS

Adams et al., "Chemistry of 2-Acetyl-l-pyrroline, 6-Acetyl-1,2,3,4-tetrahydropyridine, 2-Acetyl-2-thiazoline, and 5-Acetyl-2,3-dihydro-4H-thiazine: Extraordinary Maillard Flavor Compounds," Chem. Rev., vol. 106, pp. 2299-2319, 2006.

Singh et al., "An efficient one-pot synthesis of pyrrolines and tetrahydropyridines from their chloro-precursors via in situ aza-Wittig reaction," Tetrahedron Letters, vol. 46, pp. 4213-4217, 2005.

Favino et al., "Penicillin Acylase-Mediated Synthesis of 2-Acetyl-1-pyrroline and of 2-Propionyl-1pyrroline, Key Roast-Smelling Odorants in Food. Inclusion Complexes with β-Cyclodextrin and Their NMR and MS Characterization," J. Org. Chem., vol. 61, pp. 8975-8979, 1996.

De Kimpe et al., "Syntheses of the Principal Bread Flavor Component, 6-Acetyl-1,2,3,4-tetrahydropyridine, and Acetal Protected Precursors," Tetrahedron, vol. 51, No. 8, pp. 2387-2402, 1995.

De Kimpe et al., "Novel Syntheses of the Major Flavor Components of Bread and Cooked Rice," J. Agric. Food Chem., vol. 44, pp. 1515-1519, 1996.

Schieberle et al., "Quantitative Analysis of Aroma Compounds in Wheat and Rye Bread Crusts Using a Stable Isotope Dilultion Assay," J. Agric. Food Chem., vol. 35, pp. 252-257, 1987.

Harrison et al., "An Expeditious, High-Yielding Construction of the Food Aroma Compounds 6-Acetyl-1,2,3,4-tetrahydropyridine and 2-Acetyl-1-pyrroline," J. Org. Chem., vol. 70, pp. 10872-10874, 2005.

International Search Report issued in application No. PCT/EP2010/059007 on Jul. 30, 2010.

\* cited by examiner

METHOD FOR SYNTHESIZING 2-ACETYL-1-PYRROLINE, STABLE KETAL PRECURSORS THEREOF, AND ISOTOPICALLY MARKED ANALOGS

The present invention relates to a method for synthesizing 2-acetyl-1-pyrroline and analogs and to the use of deuterated analogs as an internal reference in an assay method and of ketal derivatives as stable precursors in a flavoring composition.

2-Acetyl-1-pyrroline (1) (referred to below as 2-AP) and its 6-membered analog, 6-acetyl-1,2,3,4-tetrahydropyridine (2) (referred to below as 6-ATHP) in equilibrium with its tautomer 6-acetyl-2,3,4,5-tetrahydropyridine (i), play a major role in the flavor of cooked products from cereal-based foods.

2-AP is a volatile molecule, which smells of popcorn, basmati rice and toasted bread. It is one of the characteristic compounds of perfumed rice (Paule and Powers, J. Food Sci., 1989, 54, 343-346), i.e. rice varieties from very restricted genetic populations and that cannot be cultivated outside their original area. It has also been identified in a large variety of other cereal products but also in several food products from both vegetal and animal origin. This molecule is also formed by Maillard reactions (including from proline and glutamic acid) during the cooking of rice or other cereal-based foods such as toasted bread, popcorn, sesame seeds, etc. This compound, like many heterocycles, has a strong olfactory power, with a detection threshold of 0.02 ng/L in air and 0.1 µg/Kg in water (Adams and De Kimpe, Chem. Rev., 2006, 106, 2299-2319). Therefore 2-AP can be extensively used for flavoring food products, such as bakery products, toasted or cooked foods, beverages (tea, coffee), either to enhance the toasted character or as a modifier in flavored formulations. However, this molecule is fragile and may need to be stabilized in some applications. Furthermore, 2-AP is generally present in very low concentration in foods, as evaluated from 6 to 90 ppb, in 10 different varieties of raw rice, by steam stripping combined with continuous extraction (Buttery et al., J. Agric. Food Chem., 1983, 31, 823-826). However, the instability of this compound and its low content makes it difficult to be assayed, and this explains why numerous extraction and assay methods have been experimented, which vary according to the medium (Shieberle and Grosch, J. Agric. Food Chem., 1987, 35, 252-257; Yoshihashi et al., J. Agric. Food Chem., 2002, 50(7), 2001-2004; Hoffman and Schieberle, J. Agric. Food Chem., 1998, 46, 616-619 and 2270-2277).

In turn 6-ATHP is the major flavoring component in bakery products. This molecule was also identified in crisps, popcorn and bread crust (Demyttenaere et al., The chemistry of the most important Maillard flavor compounds of bread and cooked rice, In "Heteroatomic aroma compounds", ACS symposium series 826, Ed. Reineccius Ga., Reineccius TA., Washington, 2002, 150-160). It also has a typical toasted smell, close to that of popcorn, yet with a lower olfactory power than that of its lower counterpart: 0.06 ng/L in air and 1 µg/Kg in water (Adams and De Kimpe, Chem. Rev., 2006, 106, 2299-2319).

Also included in the same class are 2-propionyl-1-pyrroline (2PP) or its higher counterpart, 2-propionyl-3,4,5,6-tetrahydropyridine, having a characteristic smell of toasted foods (Adams and De Kimpe, Chem. Rev., 2006, 106, 2299-2319).

2-propionyl-1-pyrroline (2PP)    2-Propionyl-3,4,5,6-tétrahydropyridine

The first synthesis of 2-AP was carried out by Buttery's team (Buttery et al., J. Agric. Food Chem., 1983, 31, 823-826) by oxidation of 2-(1-hydroxyethyl)pyrrolidine in the presence of a large excess of silver carbonate over celite. However, this synthesis is disadvantageous in that it employs a quite costly catalyst, i.e. rhodium/alumina. Also, deuterium-labeling of the molecule is difficult to envisage by such a synthetic route.

Two possible ways of preparing 2-AP were also described by De Kimpe (De Kimpe et al., J. Agric. Food Chem., 1993, 41, 1458-1461). The first way uses pyrrolidine as a starting material and results in 2-AP or its deuterated analog (with the use of $CD_3MgI$ reacted with the nitrile derivative) being formed. This synthesis is however disadvantageous in that it employs a relatively dangerous product that is cyanhydric acid. The second synthetic route was developed from proline but it was difficult to optimize the separation of the final products from the resulting mixture. In 1991, De Kimpe (EP 0 436 481) was already describing not only the synthesis of 2-AP from pyrrolidine but also the preparation of 6-ATHP from piperidine according to the same oxidation method of the amine to imine followed by cyanation, then oxidation into 2 cyano-1-azacycloalkenes and finally reaction with a Grignard reactant.

2-AP was also synthetized by Rewicki et al. (Progress in Flavor Precursor Studies; Schreier P., Winterhalter P. Eds.; Allured Publishing Corp.: Carol Stream, 1993, p 301) by an intramolecular aza-Wittig type cyclisation involving azidodiketone. This dicarbonylated γ-azido precursor was formed by a series of reactions comprising addition of trimethylsilyl cyanide onto an α,β-unsaturated aldehyde, α-deprotonation of the nitrile followed by alkylation, desilylation and ozonolysis. However, this synthesis is difficult to implement and involves potentially toxic reactants. Likewise, 2-acetyl-3,4,5,6-tetrahydropyridine could be prepared, as in Rewicki et al. DE 42 17 395, by an aza-Wittig type reaction involving cyclisation of 7 azidoheptan-2,3-dione obtained through multistep synthesis. De Kimpe and Stevens (Tetrahedron, 1995, 51, 2387-2402) also developed such approach consisting of a cyclisation of aza-Wittig type from an azide precursor resulting from the chlorinated derivative, i.e. 7-chloro-2,2-dimethoxyheptan-3-one. Singh et al. (Tetrahedron Letters, 2005, 46, 4213-4217) described, on the same principle, the synthesis of 6-ATHP from the same halogenated intermediate, 7-chloro-2,2-dimethoxyheptan-3-one. In this more recent study however, the reaction takes place under microwave activation.

De Kimpe and Keppens (J. Agric. Food Chem., 1996, 44 (6), 1515-1519) also developed a method for synthesizing 2-AP from a vicinally positioned diimine obtained from butane-2,3-dione and isopropylamine in the presence of titanium chloride. This makes it possible to obtain 6-amino-2,3-hexadione which spontaneously cyclizes to give 2-AP together with 6-methyl-2,3,4,5-tetrahydropyridin-5-one. The use of this method of synthesis is however limited by the difficulty in separating those two compounds.

In the same year, Favino et al. (J. Org. Chem., 1996, 61, 8975) developed another method for synthesizing the same terminally-aminated α-dione, protected by a benzyloxy moiety. Enzyme hydrolysis of this compound by an immobilized acylase results in the primary amine, which spontaneously cyclizes to form 2-AP. However it may be assumed that the cyclisation does not exclusively lead to 2-AP like in the method described above.

Hofmann and Schieberle (J. Agric. Food Chem., 1998, 46, 616-619 and 2270-2277) provide a new method of synthesis from t-butyloxycarbonyl-protected (Boc-protected) proline. They achieve the three-step synthesis of 2-acetylpyrrolidine through forming a thioester, introducing the methyl moiety by addition of methylmagnesium bromide, then deprotecting the aminated moiety with trifluoroacetic acid. The 2-acetylpyrrolidine, obtained as a trifluoroacetate salt, spontaneously oxidizes into 2-acetyl-1-pyrroline after adjusting the pH back to 7 with addition of an alkaline solution. This synthesis however has the drawback that it uses organomagnesium compounds, which are readily hydrolysable and thus difficult to handle.

Another way to obtain 2-acetyl-1-pyrroline involving a protection step of the ring nitrogen was proposed recently by Harrison and Dake (J. Org. Chem., 2005, 70, 10872-10874). These authors provide a synthesis strategy from pyrrolidin-2-one involving ring-opening by a vinyl lithium followed by cyclisation in an acidic medium. 2-AP is released after deprotection of the aminated moiety, together with 6-methyl-2,3, 4,5-tetrahydropyridin-5-one. The use of this method of synthesis is however limited by the difficulty in separating those two compounds.

Fuganti et al. (Tetrahedron, 2007, 63, 4762-4767) disclose a method of synthesis of 2-AP and 6-ATHP by oxidation during the final key step of cyclic imine precursors. The drawback of this synthesis is the use of selenium dioxide, a toxic oxidizing agent.

Patent application EP 0 545 085 discloses a synthetic route starting from N-(trimethylsilyl)butyrolactam in the presence of 1-ethoxyvinyl lithium at very low temperature followed by a 7-day acid hydrolysis resulting in 2-acetyl-1-pyrroline and its tautomer which are difficult to separate.

U.S. Pat. No. 6,723,856 claims a 3-step synthetic route to 2-acetyl-1-pyrroline from proline. The synthesis goes through its methyl ester that is oxidized at 0° C. to give the pyrroline ring, and subsequent addition of an organomagnesium compound results in the desired compound. As for the method described by De Kimpe et al. in 1993, it can be expected that several adducts will be formed during the last step and that the use of deuterated methylmagnesium bromide would lead to a molecule labeled on exchangeable position.

In 2007, Yukawa and Murakami (JP 2007/153785) provided another synthetic route starting from proline which also involved a methyl esterification in the presence of $SOCl_2$ at −5-10° C., followed by a N-chloration with $Me_3COCl$, and then a dehydrochloration in the presence of triethylamine, and finally a Grignard reaction with MeMgI. The reaction crude product is taken up with ethanol and subjected to azeotrope distillation. It is to be noted however that the N-chloration step is difficult to implement.

Thus, the methods of synthesis of 2-AP of the prior art have several drawbacks: first of all some methods use toxic materials that are difficult to envisage for the use of the final products in the agri-food sector, the final product is often difficult to separate from other products formed during the last step (such as its tautomer) and lastly, some syntheses do not make it possible to provide isotopically labeled analogs in a non-exchangeable position.

The inventors of the present invention have therefore developed a new method of synthesis overcoming these drawbacks, and thus easy to implement at low cost, with a minimum number of steps, and providing easy purification of the final molecules, without employing materials which are toxic or prohibited by the agri-food industry and using naturally existing compounds as a starting material (including glutamic acid or 2-aminoadipic acid). This synthesis method offers the additional benefit of readily providing isotopically labeled (deuterium-labeled) compounds in particular for the use as an internal reference in an assay method. Furthermore it involves ketal derivatives, as synthesis intermediates, that represent stable precursors for flavoring compounds in order to overcome the stability issue raised by such molecules. In fact, the ketal derivatives can be stably kept if they are protected from air and moisture, and then can gradually release the flavoring molecules, under the action of water followed by oxygen.

As its first object, the present invention thus primarily relates to a method for synthesizing a compound of the following formula (I):

(I)

wherein:

R is a methyl or ethyl group, n is 1 or 2, and

X is a $CH_2$ or $CD_2$ group, from a compound of the following formula (II):

(II)

wherein R and n are as defined above, comprising the following series of steps:
(a) optionally protecting the exocyclic carbonyl function of the compound of the formula (II) to provide a compound of the following formula (III):

(III)

wherein:
R and n are as defined above, and
Z represents a protected carbonyl moiety, in particular in the form of a ketal of the formula $C(AR^1)(AR^2)$, where A represents an oxygen or sulfur atom and $R^1$ and $R^2$ represent, independently from each other, a $(C_1-C_6)$ alkyl group, such as ethyl, or $R^1$ and $R^2$ taken together form a —$(CH_2)_p$— chain connecting the atoms A carrying them, where p is 2 or 3,
(b) reducing the compound of the formula (II) or the formula (III) such as defined above in the presence of hydride or deuteride ions, and in particular in the presence of $LiAlH_4$ or $LiAlD_4$, to provide a compound of the following formula (IV):

(IV)

wherein X, n and R are as defined above, and $Z^1$ is Z as defined above or is a CHOH or CDOH group,
(c) optionally deprotecting the protected exocyclic carbonyl function of the compound of the formula (IV) obtained from the previous step in which $Z^1$=Z, to provide a compound of the following formula (V):

(V)

wherein X, n and R are as defined hereinabove, and
(d) oxidizing the compound of the formula (IV) or the formula (V) as defined above, in particular in the presence of oxygen, to provide a compound of the formula (I).

Within the meaning of the present invention, the term <<$(C_1-C_6)$alkyl>> is defined as a linear or branched, saturated hydrocarbon chain comprising 1 to 6, preferably 1 to 4, carbon atoms. Examples of alkyl groups include, but are not limited to, methyl, ethyl, n-propyl, isopropyl, sec-butyl, tert-butyl, n-butyl, isobutyl, n-pentyl and n-hexyl groups. Particularly preferred is an ethyl or a methyl group.

Step (a):
This step is to protect the exocyclic carbonyl function to prevent its reduction during the next step (b).
The term <<protected moiety>> refers to, within the meaning of the present invention, a moiety for selectively blocking a reactive site in a multifunctional compound so that a chemical reaction can be carried out selectively at another non-protected reactive site within the definition traditionally relating thereto in synthetic chemistry.

Within the meaning of the present invention, the term <<protected carbonyl moiety>> is defined as any group for protecting a carbonyl function, and more particularly a ketone function in the present case, against unwanted reactions, such as the groups described in Greene, <<Protective Groups In Organic Synthesis>>, (John Wiley & Sons, New York (1981)) and Harrison and al. <<Compendium of Synthetic Organic Methods>>, Vols. 1 to 8 (J. Wiley & Sons, 1971 to 1996). It may be in particular a ketal or a thioketal moiety of the formula $C(AR^1)(AR^2)$ as defined above. Preferably, A will represent an oxygen atom. The ketal moiety can be in particular $C(OEt)_2$.

Step (b):
The conditions for carrying out such a reduction step are well known by those skilled in the art. Reducing the amide function, together with reducing the ketone function if the latter is not protected, can be done in the presence of hydride or deuteride ions.

The reactants which are useful for carrying out this reduction can be in particular $LiAlH_4$ or $LiAlD_4$.

Advantageously, this reaction is carried out in a solvent such as diethyl ether, preferably at 0° C.

By using deuteride ions it is possible to introduce onto the molecule two deuterium atoms in the alpha position to the nitrogen atom. The presence of such atoms can be useful in an assay method as described hereinafter, in particular since these atoms are not exchangeable with hydrogen atoms (as opposed to the alpha position of the carbonyl), thus maintaining the isotopic labeling.

Step (c):
Step (c) will only be carried out if step (a) has been carried out, that is if the exocyclic carbonyl has been protected. The conditions for carrying out this step will thus depend on the type of group selected for protecting the ketone and will be readily determined by those skilled in the art.

In the case where the ketone would have been protected in the form of a ketal of the formula $C(AR^1)(AR^2)$ such as defined above, the deprotection can be done by treatment in an acidic medium, in particular in the presence of aqueous hydrochloric acid.

Step (d):
The conditions for oxidizing the amine function to imine and if necessary the alcohol to ketone are well known by those skilled in the art.

Thus, simultaneous oxidation of the amine and the alcohol can be carried out by a Dess-Martin reaction. This reaction takes place advantageously under an inert atmosphere, in particular under argon or nitrogen atmosphere, and advantageously at room temperature, in particular in a solvent such as diethyl ether.

In the case where the exocyclic ketone function is unreacted, the inventors could have found that the resulting compound was spontaneously oxidized in the open air (that is by oxygen present in the air) or by bubbling oxygen through a reaction mixture at pH=7.

The resulting final compound can be extracted from the reaction mixture by techniques well known by those skilled in the art and be purified if need be.

As the products obtained are very volatile compounds, they can be isolated and purified by distillation.

The compound of the formula (II), used as a starting material in the above-mentioned method, can in turn be prepared from a compound of the following formula (VI):

(VI)

wherein n is as defined above,
by a Dakin-West reaction in the presence of an anhydride of the formula $(RCO)_2O$,
where R is as defined above, followed by an alkaline treatment.

Thus, the synthesis can be carried out starting from glutamic acid when n=1 or from 2-aminoadipic acid when n=2, both of which are commercially available compounds and of natural origin.

The conditions for carrying out the Dakin-West reaction are well known by those skilled in the art. This reaction provides for the cyclisation of the compound of the formula (VI) into a 5-(when n=1) or 6-(when n=2) membered nitrogen-containing ring, with acylation, and in particular simultaneous acetylation, at positions 1 and 5 (when n=1) or 6 (when n=2).

This reaction is advantageously carried out in an alkaline medium, in particular in the presence of triethylamine, in acetic anhydride (where R=Me) or propanoic anhydride (where R=Et), in the presence of a catalytic amount of DMAP (N,N-dimethyl-4-aminopyridine). Preferably, the reaction will be carried out while hot, at a temperature of about 60° C.

As this reaction produces the N-acylated derivative, it is then necessary to conduct a hydrolysis step in order to obtain the free amine function, in particular through an alkaline treatment, in particular in the presence of $K_2CO_3$, as indicated in the reaction scheme below.

According to one particular embodiment of the invention, the method will comprise the following series of steps:
(a1) protecting in the form of a ketal the exocyclic carbonyl function of a compound of the formula (II) as defined above,
to provide a compound of the following formula (IIIa):

(IIIa)

wherein n, A, R, $R^1$ and $R^2$ are as defined above, (b1) reducing the compound of the formula (IIIa) obtained from the previous step in the presence of hydride or deuteride ions, and in particular in the presence of $LiAlH_4$ or $LiAlD_4$, to provide a compound of the following formula (IVa):

(IVa)

wherein X, A, n, R, $R^1$ and $R^2$ are as defined above,
(c1) deprotecting the protected exocyclic carbonyl function of the compound of the formula (IVa) obtained from the previous step to provide a compound of the formula (V) as defined above, and
(d1) oxidizing the compound of the formula (V) obtained from the above, in particular in the presence of oxygen, to provide a compound of the formula (I).

The above-mentioned comments relating to steps (a), (b), (c) and (d) apply to steps (a1), (b1), (c1) and (d1) described above, respectively.

This method of the invention is particularly suitable for preparing compounds of the formula (I) in which R represents a methyl group and in particular for the following compounds: 2-acetyl-1-pyrroline, 2-acetyl-1-pyrroline-5,5-$d_2$ and 6-acetyl-1,2,3,4-tetrahydropyridine.

The present invention provides, as a second object, a compound of the following formula (Ia):

(Ia)

wherein:
R is a methyl or ethyl group, and
n is 1 or 2.

Such a compound can be useful as an internal reference in an assay method as described below and can be in particular 2-acetyl-1-pyrroline-5,5-$d_2$.

The present invention thus provides, as a third object, the use of a compound of the formula (Ia) as described above, as an internal reference in a method for assaying a compound of the following formula (Ib):

(Ib)

wherein:
R is a methyl or ethyl group, and
n is 1 or 2.

The particular feature of the deuterated analogs of the formula (Ia) is their deuteration on the ring, which prevents exchange reactions, such as those that can be seen with those compounds that are deuterated in the α position of the exocyclic carbonyl, that is in the group represented by R, and which generates, in mass spectrometry, characteristic residues readily used in methods of isotope dilution assay. The compounds of the formula (Ia) can thus be used as internal references for the determination of natural heterocycles of the formula (Ib) in complex natural environments.

In particular, the 2-acetyl-1-pyrroline-5,5-$d_2$ can be used as an internal reference for the determination of 2-acetyl-1-pyrroline, in particular in rice.

Thus, the present invention provides, as a fourth object, a method for assaying a compound of the formula (Ib) as defined above using a compound of the formula (Ia) as defined above, as an internal reference.

Such an assay method using internal reference is used in chromatography for carrying out a quantitative analysis. Whereas it can be applied to various types of detectors, an increased sensibility is obtained with mass spectrometer detectors, targeting specific ionic residues with SIM (Selected Ion Monitoring) mode acquisition (K. Ellendt and al., SOFIW J. 2001, 127, 29-34), or applied in chromatography-tandem MS/MS. The assay method using internal reference is based on the individual comparison of the peak obtained for the compound to be quantified against the peak obtained for the reference material suitably selected and added in a known amount to the mixture to be analyzed. The amount of the compound to be quantified is then determined using a <<response>> curve of said compound to be assayed compared with the reference material that will have been calculated independently and prior to the assay, this step requiring the use of both test molecules (the compound to be assayed and the reference material) (E. Cicchetti and al., Flavour Fragrance Journal, 2008, 23, 450-459). Furthermore, when assaying a compound present in a complex matrix requiring a specific extraction (as may be the case for the compounds of the formula (I) of the present invention), accurate quantification recommends the use of a labeled counterpart as an internal reference. This technique, that is referred to as <<Stable isotope dilution assay>> (SIDA), makes it possible to eliminate the matrix effect during extraction and any change of experimental conditions.

The compound of the formula (Ib) can particularly be 2-acetyl-1-pyrroline with as an internal reference 2-acetyl-1-pyrroline-5,5-$d_2$ as a compound of the formula (Ia).

The present invention provides, as a fifth object, a compound of the following formula (IVa):

(IVa)

wherein:
R is a methyl or ethyl group,
n is 1 or 2,
X is a $CH_2$ or $CD_2$ group,
A represents an oxygen or sulfur atom, and
$R^1$ and $R^2$ represent, independently from each other, a ($C_1$-$C_6$)alkyl group, such as ethyl, or $R^1$ and $R^2$ taken together form a —$(CH_2)_p$— chain connecting the atoms A carrying them, where p is 2 or 3.

Preferably, A will represent an oxygen atom and the group represented by $C(AR^1)(AR^2)$ can be in particular a $C(OEt)_2$ group.

The group represented by R can be in particular a methyl group and the compound of the formula (IVa) can be selected in particular from amongst:

The present invention provides, as a sixth object, a flavoring composition comprising a compound of the formula (IVa) as defined above, in which X=$CH_2$.

Preferably, A will represent an oxygen atom in the formula (IVa) and the group represented by $C(AR^1)(AR^2)$ can be in particular a $C(OEt)_2$ group.

The group represented by R can be in particular a methyl group and the compound of the formula (IVa) can be the following compound:

wherein n is as defined above and is in particular 1.

In fact, the low stability of 2-acetyl-1-pyrroline makes it difficult to use it on an industrial scale (Zviely, Perfum. Flay., 2006, 31, 20-35). On the other hand, its stable precursor, the aminoketal of the formula (IVa), which is readily hydrolyzed in weakly acid or neutral media, with spontaneous oxidation in the presence of oxygen, can be used as a precursor of flavoring molecules, in particular in the agri-food sector. Thus, providing that the flavoring composition is prevented from any risk of acid hydrolysis and from any contact with air, and more particularly with the oxygen in the air, it remains stable and can easily be stored. After having come into contact with air, it can release the 2-acetyl-1-pyrroline gradually and in a controlled way.

The present invention thus provides, as a seventh object, the use of a compound of the formula (IVa) as defined above, in which X=$CH_2$ and A=O, for flavoring a food product, preferably wherein the compound of the formula (IVa) corresponds to the following formula:

As mentioned above, the flavoring is obtained by forming a compound of the formula (Ib) as defined above, from the compound of the formula (IVa) (by acid hydrolysis followed by oxidation in contact with air), in particular by time-controlled forming of the compound of the formula (Ib).

The present invention also provides, as an eighth object, a method for preparing a compound of the formula (IVa) as defined above, characterized in that it comprises the following series of steps:

(a2) protecting in the form of a ketal the exocyclic carbonyl function of a compound of the formula (II) as defined above, to provide a compound of the formula (IIIa) as defined above, and

(b2) reducing the compound of the formula (IIIa) obtained from the previous step in the presence of hydride or deuteride ions, and in particular in the presence of LiAlH$_4$ or LiAlD$_4$, to provide a compound of the formula (IVa) as defined above.

The above-mentioned comments relating to steps (a) and (b) apply to steps (a2) and (b2) described above, respectively.

Furthermore, the compound of the formula (II) used as a starting material for the synthesis of the compounds of the formula (IVa) can be prepared from a compound of the formula (VI) as defined above, by a Dakin-West reaction in the presence of an anhydride of the formula (RCO)$_2$O, where R is as defined above, followed by an alkaline treatment.

The above-mentioned comments for said Dakin-West reaction and said alkaline treatment also apply to the present case.

This method can be used in particular for preparing a compound of the formula (IVa) selected from:

The present invention can be better understood in the light of the non-limiting examples given below.

EXAMPLES

1. Synthesis of Compounds of the Formula (I)

1.1. First Method for Synthesizing 2-Acetyl-1-Pyrroline and its Deuterated Analog This first synthesis was carried out according to the following reaction scheme:

N,5-diacetylpyrrolidin-2-one: 5

A 500-mL round bottom flask under argon atmosphere is charged with L-glutamic acid 4 (21 g, 0.143 mol), a catalytic amount of N,N-dimethylaminopyridine (150 mg, 1×10$^{-3}$ mol), acetic anhydride (75 mL) and triethylamine previously distilled over KOH (75 mL). The reaction mixture is maintained at 60° C. for 16 hours. The progression of the reaction is followed by TLC (eluent: ethyl acetate/petroleum ether at a ratio of 8/2). The crude reaction product is concentrated under reduced pressure (rotary evaporator and vane pump) and then taken up in 200 mL of dichloromethane; the organic layer is then washed five times with 100 mL of deionized water and then treated over animal carbon. The product obtained after evaporation of the solvent is purified by crystallization from petroleum ether/CH$_2$Cl$_2$. The crystals are rinsed with petroleum ether.

The $^1$H NMR spectrum obtained is in agreement with the reported structure of the compound.

Yield: 78%

MS: (ESI+) m/z: 170.22 [M+H]$^+$; 192.23 [M+Na]$^+$; 361.23 [2M+Na]$^+$ 5-acetylpyrrolidin-2-one: 6

In a round bottom flask, Compound 5 (2.2 g, 13×10$^{-3}$ mol) is treated with a solution of K$_2$CO$_3$ (5.6 g, 40×10$^{-3}$ mol, in 20 mL of water), with magnetic stirring at room temperature. The progress of the reaction is followed by TLC (eluent: ethyl acetate/methanol, 98/2). After stirring for 3.5 hrs, the reaction is complete. The reaction mixture is neutralized (pH=7) by adding 1N hydrochloric acid and then freeze-dried for 16 hrs. The organic residue is then extracted with $CH_2Cl_2$ (40 mL), filtered and then concentrated under reduced pressure to provide a brown viscous liquid. Purification was carried out on a silica gel column (eluent: ethyl acetate/methanol, 98/2). Compound 6 is obtained after such purification as a white powder.

The $^1H$ and $^{13}C$ NMR spectra obtained are in agreement with the reported structure of the compound.

Yield: 48%

MS: (ESI+) m/z: 128.20 $[M+H]^+$; 150.09 $[M+Na]^+$ 2-(1'-hydroxyethyl)-pyrrolidine: 7a

In a round bottom flask under argon atmosphere, Compound 6 (209 mg, $1.65 \times 10^{-3}$ mol) is treated with 4 equivalents of $LiAlH_4$ in diethyl ether (60 mL) previously distilled over sodium. The introduction of the hydride into compound 6 is carried out on an ice bath. The reaction mixture is then heated to refluxing ether. The progress of the reaction is followed by TLC (eluent: methanol/ethyl acetate, 5/5). The reaction is complete after 3 hrs. The residual hydride is decomposed with a diluted aqueous HCl solution (addition of 4 mL of a solution at pH=3). After decantation, the aqueous layer is extracted with diethyl ether (2×20 mL). The organic layers are then combined, dried over anhydrous $MgSO_4$ and concentrated under reduced pressure. A very viscous colorless liquid is obtained.

The $^1H$ NMR spectrum obtained is in agreement with the reported structure of the compound.

Yield: 92%.

MS: (ESI+) m/z: 115.85 $[M+H]^+$, 138.15 $[M+Na]^+$ 2-(1'-hydroxyethyl)-pyrrolidine (deuterated): 7b

In a round bottom flask under argon atmosphere, Compound 6 (209 mg, $1.65\ 10^{-3}$ mol; 1 equivalent) is treated with $LiAlD_4$ (276 mg, $6.58\ 10^{-3}$ mol, 4 equivalents) in diethyl ether (50 ml) previously distilled over sodium. The addition of deuteride to Compound 6 is carried out on an ice bath. The reaction mixture is then heated to refluxing ether. The progress of the reaction is followed by TLC (eluent: methanol/ethyl acetate: 5/5). After reacting for 3 hrs, the residual $LiAlD_4$ is hydrolyzed with a minimum amount of acidic water. After decantation, the aqueous layer is extracted with diethyl ether (2×20 ml). The organic layers are combined, dried over anhydrous $MgSO_4$ and then concentrated under reduced pressure. A colorless viscous liquid is obtained.

The $^1H$ NMR spectrum obtained is in agreement with the reported structure of the compound.

Yield: 94%.

MS (ESI+): m/z: 118.85 $[M+H]^+$, 141.15 $[M+Na]^+$ 2-acetyl-1-pyrroline: 1a

To 5 mL of $CH_2Cl_2$ placed in a round bottom flask under argon atmosphere are added 5 mL of Dess-Martin reactant ($1.51 \times 10^{-3}$ mol). Compound 7a (158 mg, $1.37 \times 10^{-3}$ mol) dissolved in 2 mL of $CH_2Cl_2$ is added dropwise to the reaction mixture. The progress of the reaction is followed by TLC (eluent: ethyl acetate/methanol, 8/2). When the reaction is complete (after 25 minutes), the reaction mixture is diluted with diethyl ether (10 mL) previously distilled over sodium.

In parallel, to a second round bottom flask are added 10 mL of a saturated $NaHCO_3$ solution containing sodium bisulfite (2.5 g). The reaction mixture is admixed with this solution, placed under magnetic stirring at room temperature for 10 minutes and then diluted with diethyl ether (10 mL). The organic layer is treated with a saturated $NaHCO_3$ solution (2×10 mL) followed by distilled water (2×10 mL). After phase separation, the ethereal layer is dried over anhydrous $MgSO_4$. The concentration is carried out at atmospheric pressure with cold-trapping (liquid nitrogen) of Compound 1a which is very volatile and is kept in diethyl ether at −20° C.

Figure 1:
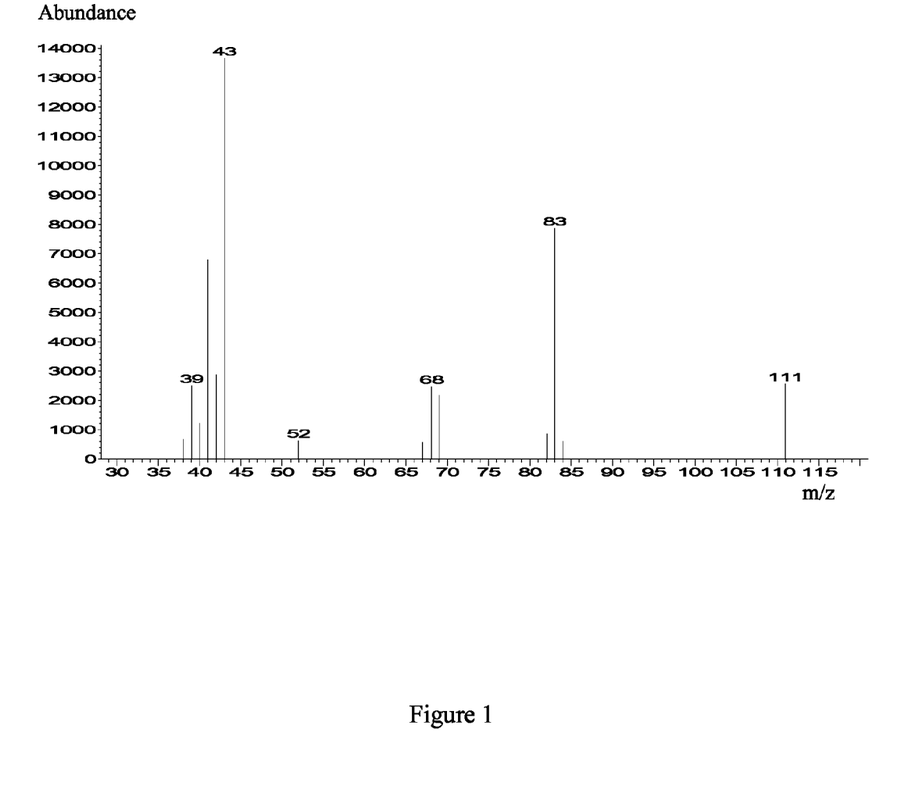
FIGS. 1, 2, 3, 4 and 5 show the electron impact mass spectra of Compounds 1a, 1b, 11, 12 and 13, respectively.

The mass and NMR spectra obtained are in agreement with the structure reported for Compound 1a. The electron impact mass spectrum is shown in FIG. 1.

2-acetyl-1-pyrroline-5,5-$d_2$: 1b

Compound 1b is prepared following the same procedure as described for the synthesis of Compound 1a with the exception that Compound 7b is used instead of Compound 7a.

Figure 2:
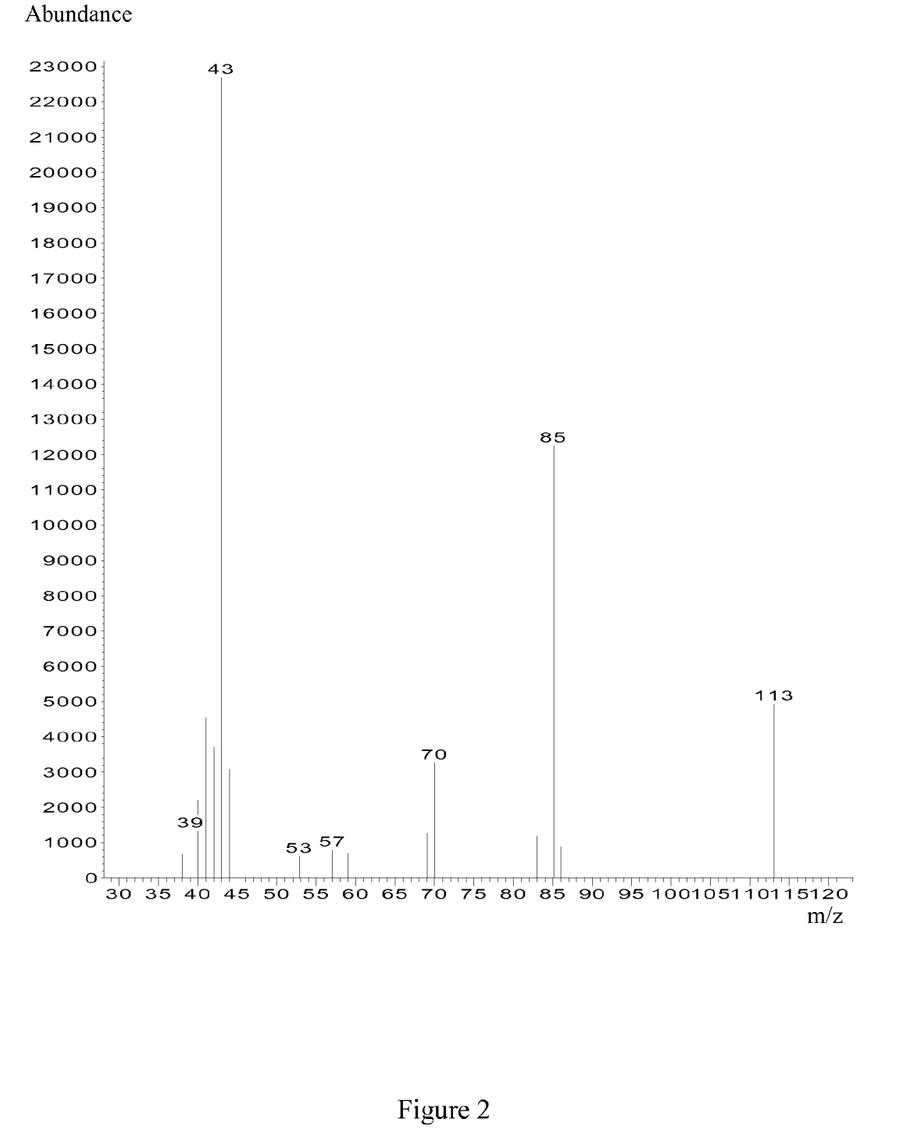

The mass and NMR spectra obtained are in agreement with the structure reported for Compound 1b. The electron impact mass spectrum is shown in FIG. 2.

1.2. Second Method for Synthesizing 2-Acetyl-1-Pyrroline

This second method of synthesis was carried out according to the following reaction scheme:

5-(1',1'-diethoxyethyl)-pyrrolidin-2-one: 11

A two-neck flask under argon atmosphere is charged with 127 mg ($1\times10^{-3}$ mol=1 eq) of 5-acetylpyrrolidin-2-one 6 in 1.1 ml of triethylorthoformate previously distilled over KOH; 330 mg of CaSO4 and 146 mg of proton exchange resin (Amberlyst 15) are added to the mixture. The latter is mixed with magnetic stirring at room temperature for 36 hours; after adding 30 mL of diethyl ether, the reaction mixture is washed rapidly with 20 mL of distilled water. The organic layer is then recovered and subsequently dried over MgSO4. After concentration under reduced pressure, the crude material is chromatographed on a silica gel column (eluent: diethyl ether/ethanol, 96/4).

Figure 3:
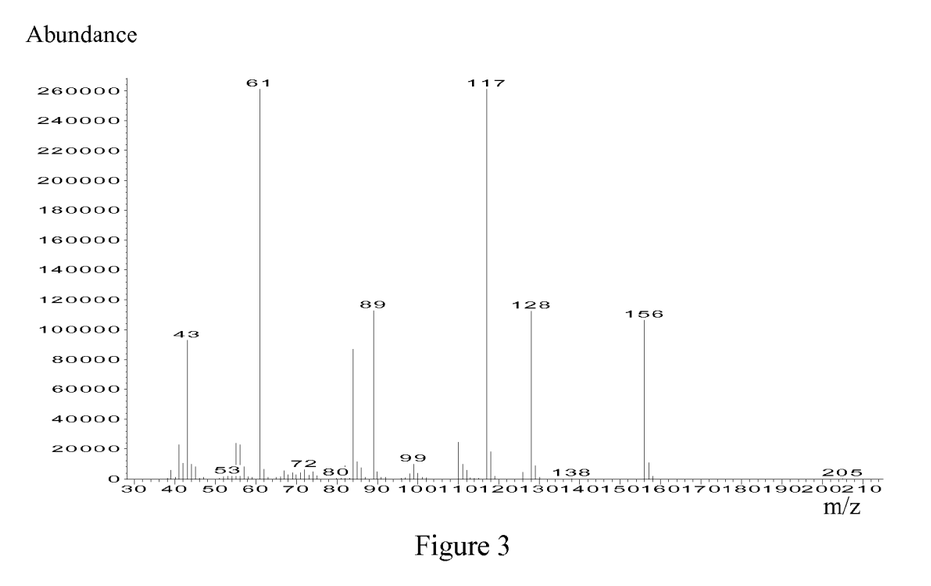

The $^1$H and $^{13}$C NMR spectra obtained are in agreement with the reported structure of the compound. The electron impact mass spectrum is shown in FIG. 3.

Yield: 36%.

Rf: 0.38 (diethyl ether/ethanol: 96/4).

MS: (ESI+) m/z: 224.28 [M+Na]$^+$; 425.48 [2M+Na]$^+$ 2-(1',1'-diethoxyethyl)-pyrrolidine: 12

A 100-mL two-neck flask under argon atmosphere is charged with 30 mL of freshly distilled diethyl ether, followed by 31 mg ($0.81\times10^{-3}$ mol, 3 eq.) of LiAlH$_4$ in powder form. Subsequently, using a graduated syringe, 56 mg ($0.27\times10^{-3}$ mol, 1 eq.) of Compound H previously dissolved in 2 mL of diethyl ether are added. The reaction mixture is left under stirring at reflux for 12 hours; hydrolysis of residual LiAlH$_4$ is then carried out with 2 mL of distilled water at neutral pH. 20 mL of diethyl ether are then added to the reaction mixture which is left under magnetic stirring for 10 minutes. After phase separation, the aqueous layer is extracted with 3×5 mL of diethyl ether. The ethereal layers are combined and concentrated under reduced pressure. A yellowish oil is obtained.

Figure 4:
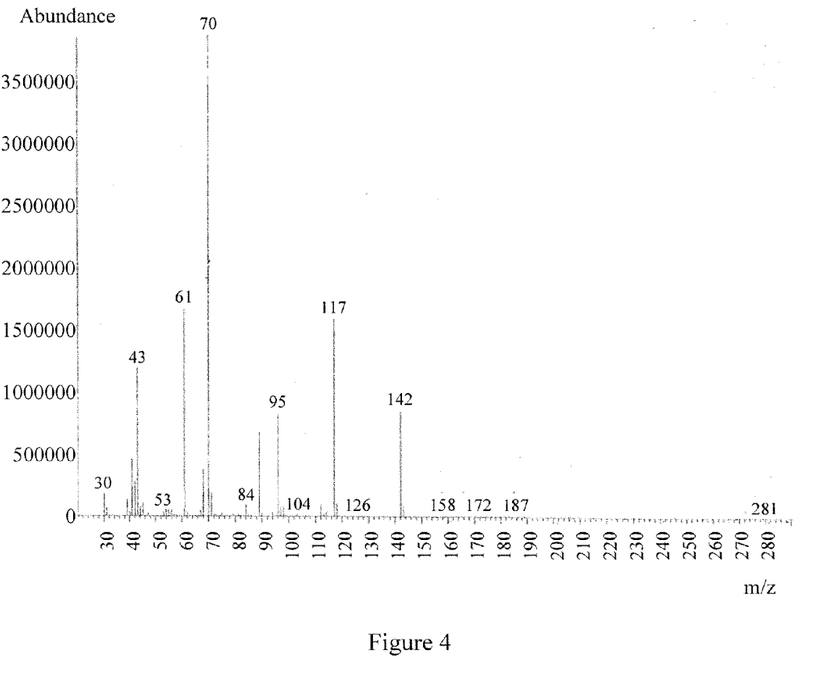

The $^1$H NMR spectrum obtained is in agreement with the reported structure of the compound. The electron impact mass spectrum is shown in FIG. 4.

Yield: 82%.

MS: (EI) m/z: 70 (100), 61 (43), 117 (41), 13 (32), 142 (22), 96 (21), 187 (M$^+$, 2).

2-(1',1'-diethoxyethyl)-pyrrolidine-5,5-d₂: 13

This compound was prepared according to the same procedure as the synthesis of Compound 12, but using LiAlD₄ instead of LiAlH₄.

Figure 5:
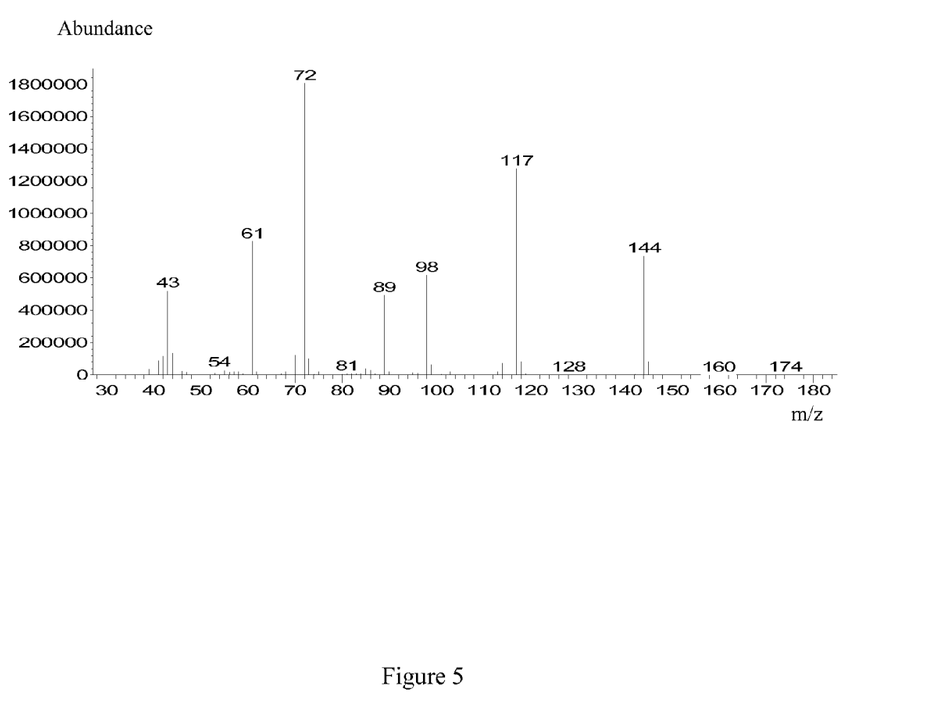

The resulting electron impact mass spectrum is shown in FIG. 5.

2-acetyl-1-pyrroline: 1a

A round bottom flask of 50 mL is charged with 38 mg of Compound 12 in a solution in 1 mL of diethyl ether; after adding 5 mL of distilled water, the reaction mixture is left under magnetic stirring for 30 min at room temperature. The pH of the solution is then brought to 3 by adding an aqueous 1N HCl solution and further stirred under magnetic stirring at room temperature for 12 hours.

The reaction mixture is then brought to pH 7 by adding an aqueous 1M NaOH solution; the round bottom flask is taken to an ice bath and oxygen is bubbled through the reaction mixture for 6 hours, with vigorous stirring. Extraction with 2 mL of diethyl ether is then carried out.

The organic layer, after drying over MgSO₄, is stored at −20° C. GC and GC/MS analyses confirm that 2-acetyl-1-pyrroline is obtained.

Yield: 22%

2-acetyl-1-pyrroline-5,5-d₂: 1b

Compound 1b was also obtained according to the same procedure as that described for the preparation of Compound 1a but using Compound 13 instead of Compound 12.

1.3. Synthesis of 6-Acetyl-1,2,3,4-Tetrahydropyridine

This synthesis was carried out using the same procedure as the synthesis described in 1.1.

N,6-diacetyl-piperidin-2-one: 8

A 50-mL round bottom flask is charged with racemic 2-aminoadipic acid (2.3 g, 1.43×10⁻³ mol) and triethylamine (7.5 mL), acetic anhydride (7.5 mL), and a catalytic amount of DMAP (15 mg). The mixture is heated to 60° C. for 24 h; the progress of the reaction is followed by TLC (eluent: ethyl acetate/petroleum ether, 8/2). Once the reaction is complete, the crude reaction product is concentrated as much as possible (rotary evaporator and vane pump) and then washed with water (5×20 mL). The water washings are extracted with CH₂Cl₂ (2×20 mL). The organic layers are combined and concentrated. Purification of 8 is carried out on a silica gel column (eluent: ethyl acetate/petroleum ether, 8/2). The fractions are dried, concentrated and the product crystallized in the form of pale yellow flakes.

The $^1$H and $^{13}$C NMR spectra obtained are in agreement with the reported structure of the compound.

Yield: 25%

MS: (ESI+) m/z: 184.25 [M+H]⁺, 206.12 [M+Na]⁺

6-acetylpiperidin-2-one: 9

Compound 8 is combined with Na₂CO₃ (4 equivalents) in water (20 mL). The mixture is stirred at room temperature and the progress of the reaction is controlled by TLC (eluent: ethyl acetate/methanol, 9/1). The reaction is complete after 4 hr. After neutralization with 1N HCl (to pH=7), the mixture is freeze-dried for 16 hrs.

The lyophilizate is taken up with CH₂Cl₂; the solution is dried over anhydrous MgSO₄ and then concentrated under reduced pressure.

The $^1$H and $^{13}$C NMR spectra obtained are in agreement with the reported structure of the compound.

Yield: 42%

MS: (ESI+) m/z: 142.03 [M+H]⁺, 164.13 [M+Na]⁺.

2-(1'-hydroxyethyl)piperidine: 10

The compound 9 obtained from the above is treated with LiAlH₄ in anhydrous diethyl ether (20 mL) under argon atmosphere. Lithium aluminum hydride (4.5 equivalents) is added to Compound 9 (11.5 mg, 8.16×10⁻⁴ mol) in a round bottom flask on an ice bath.

At the end of the addition, the reaction mixture is heated to refluxing ether. The progress of the reaction is controlled by TLC (eluent: ethyl acetate/methanol, 5/5). After 16 hrs the reaction is complete. The excess hydride is quenched by adding an aqueous acid solution (4 mL of an aqueous solution acidified to pH=3). After phase separation of the ethereal layer, the aqueous layer is extracted again with Et₂O (2×20 mL). The ethereal layers are combined, dried over anhydrous MgSO₄ and concentrated under reduced pressure on the rotary evaporator.

The $^1$H NMR spectrum obtained is in agreement with the reported structure of the compound.

Yield: 52%

6-acetyl-1,2,3,4-tetrahydropyridine: 2 and 6-acetyl-2,3,4,5-tetrahydro pyridine: 3

The reaction is carried out in an anhydrous system under argon atmosphere. A two-neck flask is charged with $CH_2Cl_2$ (3 mL) to which the Dess-Martin reactant ($4.50 \times 10^{-4}$ mol) is added as a 0.3 M solution in $CH_2Cl_2$ (i.e. 1.5 mL). Compound 10 (53 mg, $4.1 \times 10^{-4}$ mol) prepared hereinabove is solubilized in 1 mL of $CH_2Cl_2$ and added dropwise to the Dess-Martin reactant. The progress of the reaction is controlled by TLC (eluent: ethyl acetate/methanol, 8/2). After 20 minutes, as the reaction does not progress any further, 1 mL of Dess-Martin reactant is added, which leads, after 30 minutes, to complete disappearance of the amino alcohol.

The reaction mixture is then diluted with 3 mL of diethyl ether.

A saturated solution of $NaHCO_3$ (3 mL) is prepared and 0.8 g of sodium bisulfite is added. The reaction mixture is charged into this solution and the mixture is subjected to magnetic stirring for 10 minutes, then diluted with 3 mL of diethyl ether.

The organic layer is separated and then treated again with a saturated solution of $NaHCO_3$ (2×10 mL), followed by water (2×10 mL); after further phase separation, the ethereal layer is dried over anhydrous $MgSO_4$ and then concentrated by microdistillation, under atmospheric pressure, with cold-trapping (liquid $N_2$) of Compounds 2 and 3.

2. Use of 2-AP-d$_2$ for an Assay Using Internal Reference

2-Acetyl-1-pyrroline-5,5-d$_2$ (2AP-d$_2$) can be used for the quantification of natural 2-AP in various media according to an assay method by stable isotope dilution (SIDA); since the molecule is volatile, the analytical technique used will preferentially be gas chromatography optionally combined with a mass spectrometer according to various operating modes such as:

positive chemical ionization-tandem mass spectrometry (PCI-MS/MS):

The value of the method is that a strong pseudomolecular $[M+H]^+$ peak is obtained at 112 and 114 for 2AP and 2AP-d$_2$ which break up to provide the 70 and 72 ions respectively (child ions) corresponding to the ring portion of the molecule; substitution with two deuterium atoms in the 5-position of the ring can result in a two-unit difference on each of these ions that can be used to plot calibration curves.

electron impact-SIM mode (selective ion monitoring):
Using this mode of analysis the 83 and 85 target ions, which are characteristic of 2AP and 2AP-d$_2$ respectively, can be selected for plotting calibration curves.

These assay methods are advantageous in that they provide excellent sensitivity (e.g. approximately 41 ng/kg of rice with the first method).

ABBREVIATIONS

TLC Thin Layer Chromatography
DMAP N,N-Dimethyl-4-aminopyridine
ESI Electrospray ionization
GC Gas chromatography
GC/MS Gas chromatography combined with a mass spectrometer
EI Electron impact
Rf Front ratio
NMR Nuclear Magnetic Resonance
SIM Selective ion monitoring
MS Mass spectrum

The invention claimed is:

1. A compound of the following formula (IVa):

wherein:
R is a methyl or ethyl group,
n is 1,
X is a $CH_2$ or $CD_2$ group,
A represents an oxygen or sulfur atom, and
$R^1$ and $R^2$ represent, independently from each other, a ($C_1$-$C_6$)alkyl group, or $R^1$ and $R^2$ taken together form a —$(CH_2)_p$— chain connecting the atoms A carrying them, where p is 2 or 3.

2. The compound according to claim 1, wherein it is selected from:

3. A flavoring composition comprising a compound of the formula (IVa) as defined in claim 1, in which X=$CH_2$.

4. A method for flavoring a food product by adding a compound of the formula (IVa) as defined in claim 1, in which X=$CH_2$, to said food product, and forming a compound of the formula Ib to achieve said flavoring, wherein the compound (IVa) undergoes acid hydrolysis followed by oxidation in contact with air, resulting in the formation of the compound (Ib)

wherein:
R is methyl or ethyl group, and
n is 1.
5. The method according to claim 4, wherein the compound of the formula (IVa) is the compound of the formula:

6. A method for preparing a compound of the formula (IVa) as defined in claim 1, comprising the following series of steps:
(a2) protecting in the form of a ketal the exocyclic carbonyl function of a compound of the formula (II), (II)

to provide a compound of the formula (IIIa), (IIIa)

and
(b2) reducing the compound of formula (IIIa) obtained from the previous step in the presence of hydride or deuteride ions, to provide a compound of the formula (IVa), (IVa)

wherein for formulae (II), (IIIa) and (IVa)
R is a methyl or ethyl group,
n is 1,
A represents an oxygen or sulfur atom,
$R^1$ and $R^2$ represent, independently from each other, a $(C_1-C_6)$alkyl group, or $R^1$ and $R^2$ taken together form a $—(CH_2)_p—$ form a chain connecting atoms A carrying them, where p is 2 or 3, and
X is a $CH_2$ or $CD_2$ group.
7. The method according to claim 6, wherein the compound of the formula (II) is prepared from a compound of the formula (VI), (VI)

by a Dakin-West reaction in the presence of an anhydride of the formula $(RCO)_2O$, where R is a methyl or ethyl group and n is 1, followed by an alkaline treatment.
8. The method according to claim 6, wherein the compound of the formula (IVa) is selected from:

9. The flavoring composition according to claim 3, wherein the compound of formula (IVa) is 10. The method according to claim 4, wherein the compound of the formula (Ib) is formed in a time-controlled manner.
11. The method according to claim 6, wherein step b2) is carried out in the presence of $LiAlH_4$ or $LiAlD_4$.

* * * * *